(12) United States Patent
Roberts

(10) Patent No.: US 6,203,554 B1
(45) Date of Patent: Mar. 20, 2001

(54) APPARATUS, KIT AND METHODS FOR PUNCTURE SITE CLOSURE

(76) Inventor: William Roberts, R.R. #1, Box 1125, Fairfield, VT (US) 05455

(*) Notice: Subject to any disclaimer, the term of this patent is extended or adjusted under 35 U.S.C. 154(b) by 0 days.

(21) Appl. No.: 09/444,997

(22) Filed: Nov. 23, 1999

(51) Int. Cl.[7] .................................................. A61B 17/04
(52) U.S. Cl. ............................................................ 606/144
(58) Field of Search .................................. 606/139, 144, 606/147, 213, 148

(56) References Cited

U.S. PATENT DOCUMENTS

| | | | |
|---|---|---|---|
| 5,222,508 | 6/1993 | Contarini | 128/898 |
| 5,304,184 | 4/1994 | Hathaway et al. | 606/144 |
| 5,320,632 | 6/1994 | Heidmueller | 606/144 |
| 5,350,385 | 9/1994 | Christy | 606/139 |
| 5,364,408 | 11/1994 | Gordon | 606/144 |
| 5,368,601 | 11/1994 | Sauer et al. | 606/144 |
| 5,374,275 | 12/1994 | Bradley et al. | 606/144 |
| 5,391,182 | 2/1995 | Chin | 606/213 |
| 5,403,329 | 4/1995 | Hinchcliffe | 606/147 |
| 5,417,699 | 5/1995 | Klein et al. | 606/144 |
| 5,439,469 | 8/1995 | Heaven et al. | 606/144 |
| 5,462,561 | 10/1995 | Voda | 606/144 |
| 5,470,338 | 11/1995 | Whitfield et al. | 606/144 |
| 5,476,469 | 12/1995 | Hathaway et al. | 606/144 |
| 5,478,353 | 12/1995 | Yoon | 606/213 |
| 5,562,683 | 10/1996 | Chan | 606/139 |
| 5,573,540 | 11/1996 | Yoon | 606/139 |
| 5,586,986 | 12/1996 | Hinchcliffe | 606/147 |
| 5,643,292 | 7/1997 | Hart | 606/144 |
| 5,653,717 | 8/1997 | Ko et al. | 606/144 |
| 5,653,718 | 8/1997 | Yoon | 606/148 |
| 5,700,273 | 12/1997 | Buelna et al. | 606/148 |
| 5,836,955 | 11/1998 | Buelna et al. | 606/148 |
| 5,836,956 | 11/1998 | Buelna et al. | 606/148 |
| 5,846,253 | 12/1998 | Buelna et al. | 606/148 |
| 5,860,990 | 1/1999 | Nobles et al. | 606/148 |

*Primary Examiner*—Gary Jackson

(57) ABSTRACT

A puncture site closure apparatus includes a collar for being disposed on a portal sleeve extending through an opening in anatomical tissue and a pair of guide members disposed on opposite sides of the collar. The guide members are angled in directions opposite one another to form a predetermined angle with a central longitudinal axis of the collar such that lengths of suture material can be optimally inserted in the tissue through a hollow penetrating member guided through the tissue by the guide members. The puncture site closure apparatus can be provided as part of a kit including a penetrating instrument used to form an opening in anatomical tissue. A method of closing an opening in anatomical tissue through which a portal sleeve extends comprises the steps of moving a collar along the portal sleeve to position lower ends of guide members adjacent the tissue at selected locations, advancing a hollow penetrating member within one of the guide members to enter and exit the anatomical tissue, passing a length of suture material through the penetrating member so that a first end of the suture material protrudes internally of the tissue and a second end of the suture material is disposed externally of the tissue, removing the penetrating member from the tissue, drawing the first end through the portal sleeve to be disposed externally of the tissue, repeating the advancing, passing, removing and drawing steps on the other guide member to place another length of suture material in the anatomical tissue, tying the first ends together, externally of the tissue, to form a knot, passing the knot through the portal sleeve to dispose the knot internally of the tissue, withdrawing the portal sleeve from the opening, and tying the second ends together to form a knot whereby a closure is formed in the tissue.

32 Claims, 6 Drawing Sheets

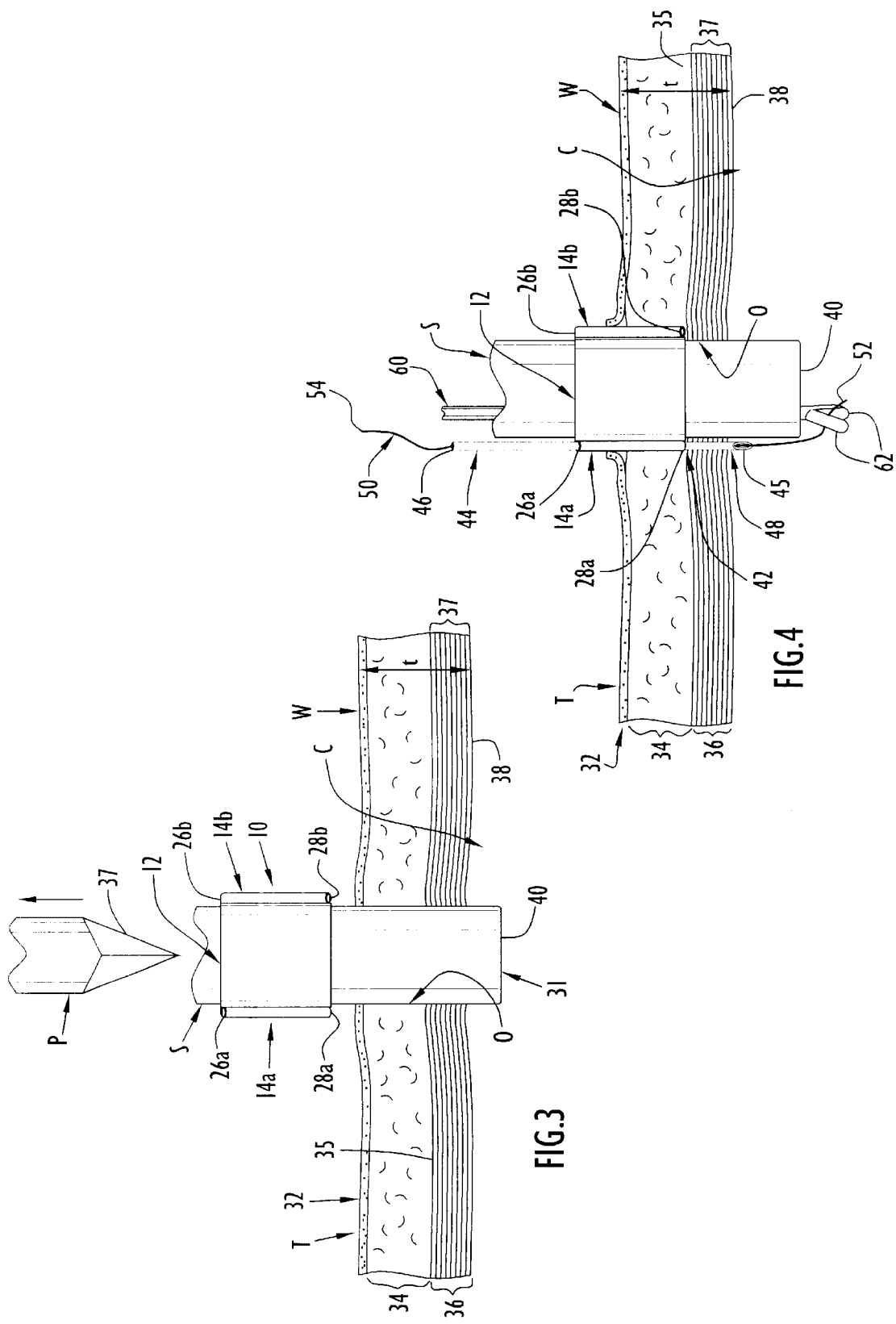

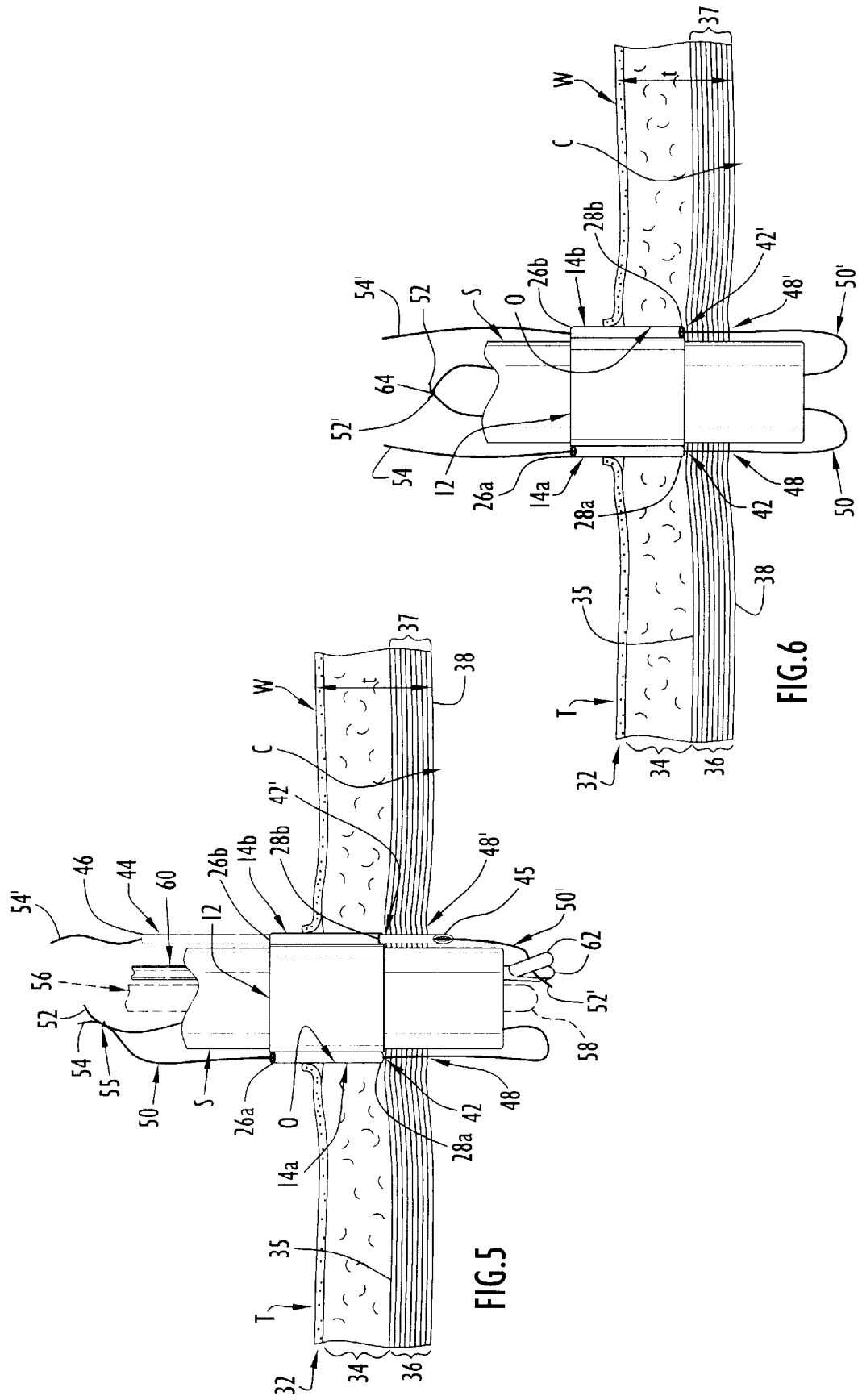

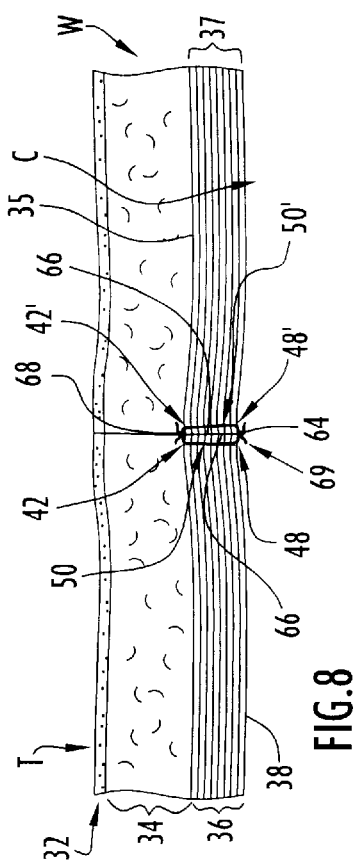
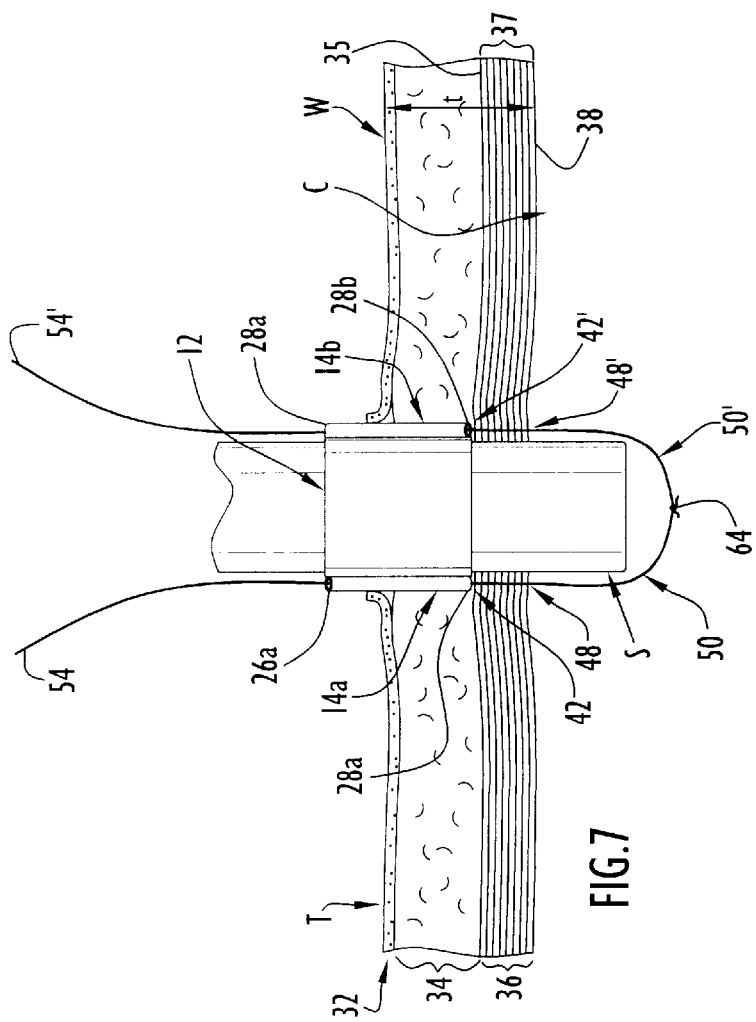
FIG.7
FIG.8

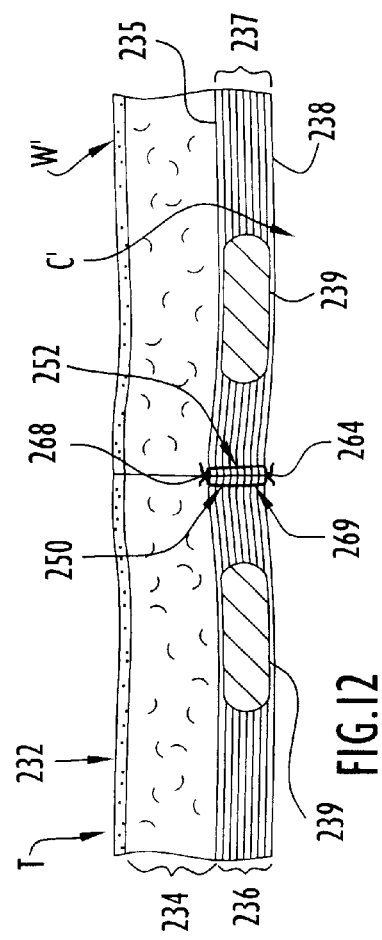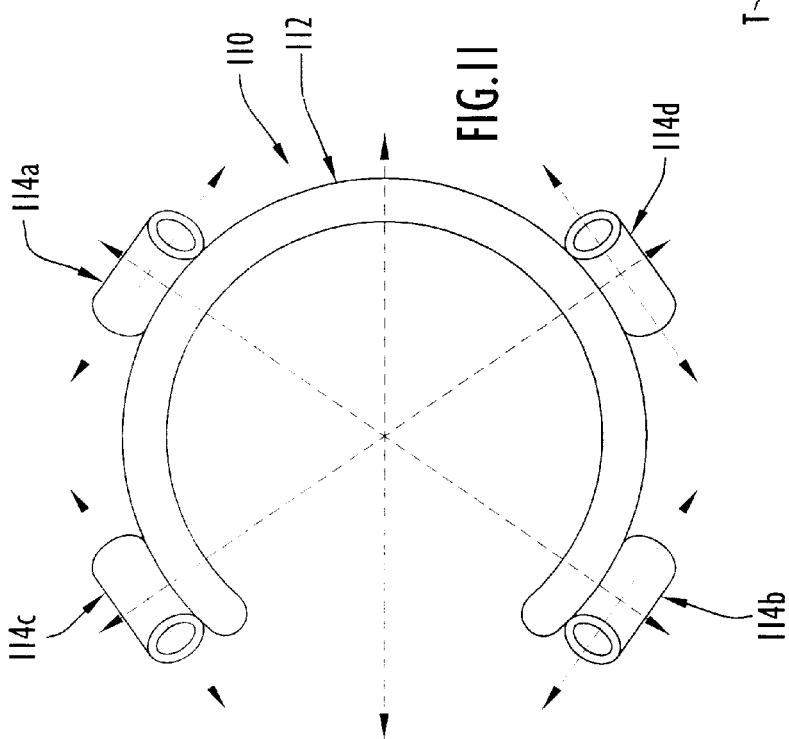

APPARATUS, KIT AND METHODS FOR PUNCTURE SITE CLOSURE

BACKGROUND OF THE INVENTION

1. Field of the Invention

The present invention relates to minimally invasive medical procedures such as endoscopy and, more particularly, to an apparatus, kit and methods for suturing puncture sites or openings created in anatomical tissue for the introduction of instruments at internal operative sites.

2. Brief Description of the Related Art

Minimally invasive medical procedures such as endoscopy and, in particular, laparoscopy and thorascopy, have become preferable over invasive medical procedures for surgery and diagnosis. Invasive or open medical procedures typically involve the creation of a relatively large vertical or longitudinal incision in anatomical tissue of a patient to access an internal operative site. Minimally invasive or closed medical procedures such as endoscopic surgery and, in particular, laparoscopic and thorascopic surgery, involve the creation of one or more small size openings or puncture sites in anatomical tissue of a patient to provide access to an internal operative site for the introduction of various instruments to be used in the operative procedure to be performed. The puncture sites or openings are typically created by inserting a penetrating instrument through the anatomical tissue, the penetrating instrument typically including an obturator disposed within a portal sleeve. When the internal operative site is located within an anatomical cavity, such as the abdomen or thorax, the obturator is inserted through the tissue of an anatomical cavity wall so as to position a distal end of the portal sleeve within the cavity. In the case of laparoscopic and thorascopic surgery, the obturator is typically inserted through the cavity wall either before or after the abdominal or thoracic cavity is distended by insufflation gas to create increased space therein. The obturator enters the abdominal or thoracic cavity wall through the skin on an external side of the abdominal or thoracic cavity wall and exits the abdominal or thoracic cavity wall through the internal fascia and parietal peritoneum or pleura on the internal side of the abdominal or thoracic cavity wall, respectively, thusly forming a puncture site or opening through the abdominal or thoracic cavity wall. The portal sleeve extends through the puncture site or opening, which corresponds or substantially corresponds in size to the external diametric or cross-sectional dimension of the portal sleeve. Upon entry of the distal end of the portal sleeve in the abdominal or thoracic cavity or other anatomical cavity or area in which the internal operative site is located, the obturator is withdrawn from the portal sleeve leaving the portal sleeve in place in the puncture site or opening to establish communication with the internal operative site One or more puncture sites or openings, each having a portal sleeve extending therethrough, can be created in the anatomical tissue or cavity wall in accordance with the number and/or type of instruments required to be introduced at the internal operative site for a particular operative procedure. Where more than one puncture site or opening is created in a patient, instruments can be introduced through the portal sleeves thereof such that more than one instrument can be present and used at the internal operative site simultaneously. Of course, it is also possible to introduce more than one instrument through a single portal sleeve so that such instruments can be present and used at the internal operative site sequentially and/or simultaneously. Exemplary instruments that may be introduced at an internal operative site through a portal sleeve or sleeves include remote viewing devices such as endoscopes or laparoscopes, grasping instruments, cutting instruments, cauterizing instruments, coagulating instruments, tissue retrieving instruments such as biopsy instruments, energy applying instruments, suturing instruments and ligating instruments which may be used individually or simultaneously during the operative procedure. Once the operative procedure has been completed, the one or more portal sleeves are withdrawn from the anatomical tissue or cavity wall, and the one or more puncture sites or openings are repaired or closed.

Minimally invasive procedures have many advantages over open procedures including reduced trauma and pain for the patient, shorter hospital stays and recovery times, fewer post-operative complications, reduced morbidity, reduced medical costs and the ability to perform many minimally invasive procedures in non-hospital sites without the need for general anesthesia. However, a drawback to minimally invasive procedures involves the difficulty associated with closing or repairing the one or more puncture sites or openings upon withdrawal of the one or more portal sleeves therefrom at the conclusion of the operative procedure.

One conventional approach to puncture site closure has involved suturing only the external and intermediate tissue layers, such as the skin and subcutaneous tissue or fat, at the puncture site or opening and leaving the inner tissue layer or layers, such as the internal investing fascia and wall musculature, unsutured such that an internal defect remains in the tissue. Where the puncture site or opening has been created to receive a portal sleeve 10 mm or less in diameter, the inner tissue layer or layers will usually naturally seal or heal in due course and close the internal defect. However, in some cases, the internal defect will not naturally seal or heal itself or will seal or heal improperly resulting in post-operative complications such as herniation, risking subsequent strangulation of the bowel or other viscera, and/or fluid migration into internal tissue layers. Where the puncture site or opening has been created to receive a portal sleeve greater than 10 mm in diameter, the relatively large size of the opening increases the risk that the inner tissue layer or layers will not properly, naturally seal or heal to close the internal defect. Accordingly, it is necessary and/or desirable, if possible, to suture or otherwise approximate and secure the inner tissue layer or layers for healing, thusly insuring proper closure of a puncture site or opening.

Another prior approach to puncture site closure, therefore, has involved conventional suturing of the inner tissue layer or layers and, in particular, the internal investing fascia and/or muscle layers, with a conventional, curved suture needle carrying a length of suture material. This is extremely difficult to accomplish in many patients due to the limited room for access and maneuverability available in minimally invasive procedures. Conventional suturing of the inner tissue layer or layers is impeded by the overall depth of the opening or puncture site, which can be considerable in heavy or obese patients due to the considerable thickness or depth of the intermediate tissue layer or layers. For example, it may be necessary for several inches of subcutaneous tissue such as fat to be retracted in order to isolate the internal investing fascia and/or muscle layers in a heavy or obese patient. The internal investing fascia in a heavy or obese patient will thusly be recessed several inches below the external side of the cavity wall, making it difficult to manually manipulate the needle between the subcutaneous tissue and the fascia.

Regardless of the patient's weight, suturing of the inner tissue layer or layers is traumatic to the patient since the puncture site or opening must be enlarged, stretched or otherwise manipulated to provide access to the inner tissue layer or layers. Where suturing is used to close the internal investing fascia of the abdominal cavity wall, poor control of the needle entering the abdominal cavity may result in puncture of the bowel or other internal organs or structure and may result in inadvertent securement of the bowel or other internal organs or structure in the sutured fascial closure. Because the surgeon cannot directly visualize the exact position of the needle until after it has passed through the cavity wall into the anatomical cavity, several insertions of the needle may be necessary to place the needle at the optimal distance from the puncture site in order to grasp or stitch the appropriate amount of tissue. The needle used for suturing may be inadvertently dropped in the anatomical cavity, with the needle possibly becoming lost and/or damaging anatomical tissue or structure within the cavity. The needle may break during suturing, with possible loss of a needle fragment or fragments in the anatomical cavity and/or damage to tissue or structure within the cavity caused by the needle fragment or fragments. Suturing of the inner tissue layer or layers is tedious and time consuming for the surgeon and increases the time required to perform minimally invasive surgical procedures. Given the increasing use of minimally invasive procedures and the use of larger portal sleeves, the occurrence of complications associated with puncture site closure can be expected to increase.

Various apparatus and methods have been proposed to facilitate the closure of puncture sites or openings in minimally invasive procedures as represented by U.S. Pat Nos. 5,222,508 to Contarini, 5,304,184 to Hathaway et al, 5,320,632 to Heidmueller, 5,350,385 to Christy, 5,364,408 to Gordon, 5,368,601 to Sauer et al, 5,374,275 to Bradley et al, 5,391,182 to Chin, 5,403,329 to Hinchcliffe, 5,417,699 to Klein et al, 5,439,469 to Heaven et al, 5,462,561 to Voda, 5,470,338 to Whiffield et al, 5,476,469 to Hathaway et al, 5,478,353 to Yoon, 5,562,683 to Chan, 5,573,540 to Yoon, 5,586,986 to Hinchcliffe, 5,643,292 to Hart, 5,653,717 to Ko et al, 5,653,718 to Yoon, 5,700,273 to Buelna et al, 5,836,955 to Buelna et al, 5,836,956 to Buelna et al, 5,846,253 to Buelna et al and 5,860,990 to Nobles et al.

Many of the prior apparatus for puncture site closure utilize suture needles and suture material incorporated in complex mechanical structures that are physically cumbersome and/or operationally complicated. Furthermore, many of the prior apparatus and methods for puncture site closure require that the suture needles and/or other parts of the apparatus be introduced a significant distance or depth internally of the tissue being sutured. Accordingly, there is a significant risk that the suture needles and/or other parts of the apparatus will penetrate or injure internal organs or other structures. In addition, many prior apparatus and methods for puncture site closure present the risks of dropped, lost and/or broken suture needles. Many prior apparatus for puncture site closure cannot be used with a portal sleeve in place in the puncture site. Some prior apparatus for puncture site closure can only be used subsequent to removal of the portal sleeve and, therefore, in absence of a pneumoperitoneum, thusly increasing the risk of internal injury since the anatomical cavity will no longer be distended.

Prior apparatus and methods for closing puncture sites or openings in minimally invasive procedures generally require specially designed or customized suture needles or other equipment not normally found in operating rooms. Additionally, conventional apparatus for puncture site closure commonly require that the suture material be pre-loaded into an instrument or other device and/or that the suture material be preformed with loops and/or knots. Some prior apparatus for puncture site closure necessitate the use of anchors on the suture material. There is also a tendency with prior apparatus and methods for puncture site closure for the suture material to become inadvertently tangled during use. Prior apparatus for puncture site closure are not easily adjustable to accommodate different thicknesses of anatomical tissue and generally fail to provide for insertion of the suture material in the tissue at an optimal location for a particular tissue thickness. The efficacy of prior apparatus and methods for puncture site closure undesirably depends to a great extent on the individual skill or expertise of the surgeon such that consistently favorable results are not obtained therewith by surgeons of varying degrees of skill and experience.

Accordingly, the need exists for a simplified apparatus, kit and methods for puncture site closure that allow one or more inner tissue layers at a puncture site or opening to be closed via sutures placed in the one or more inner tissue layers while a portal sleeve is disposed within the puncture site or opening. The need also exists for an apparatus, kit and methods for puncture site closure wherein a suture is guided by a puncture site closure apparatus for placement in one or more inner tissue layers at an optimal location. There is also a need for an apparatus, kit and methods for puncture site closure wherein the puncture site closure apparatus is easily adaptable for different thicknesses of anatomical tissue to insure optimal placement of a suture in one or more inner layers of the anatomical tissue in accordance with the particular tissue thickness. An additional need exists for an apparatus, kit and methods for puncture site closure that are used in conjunction with conventional penetrating members or needles, conventional suture materials and conventional grasping instruments typically available in operating rooms. The need further exists for an apparatus, kit and methods for closing puncture sites wherein the distance or depth that the apparatus extends internally of the tissue being sutured is minimized to avoid injury to internal organs or other anatomical structures and wherein loss of needles or needle fragments is avoided. Yet a further need exists for an apparatus, kit and methods for puncture site closure capable of obtaining consistently favorable results by surgeons of varying degrees of skill and experience.

SUMMARY OF THE INVENTION

Accordingly, it is a primary object of the present invention to overcome the aforementioned disadvantages of prior apparatus and methods for puncture site closure.

Another object of the present invention is to place a suture in one or more inner layers of anatomical tissue at a puncture site or opening in the anatomical tissue while a portal sleeve is disposed within the puncture site or opening.

A further object of the present invention is to place a suture in the inner layers of the abdominal cavity wall at a puncture site or opening in the abdominal cavity wall while a portal sleeve extends through the puncture site or opening into the abdominal cavity.

An additional object of the present invention is to place a suture in the inner layers of the abdominal cavity wall at a puncture site or opening in the abdominal cavity wall while a pneumoperitoneum is maintained in the abdominal cavity.

Still another object of the present invention is to place a suture in inner layers of the thoracic cavity wall at a puncture site or opening in the thoracic cavity wall while a portal sleeve extends through the puncture site or opening into the thoracic cavity.

It is also an object of the present invention to suture a selective thickness of anatomical tissue, including inner tissue layers thereof, at a puncture site or opening in the anatomical tissue using an apparatus easily operated and/or executed by surgeons of varying degrees of skill and experience.

The present invention also has as an object to optimally place a suture in one or more inner layers of anatomical tissue at a puncture site or opening in the anatomical tissue in order to form a closure of desired strength.

Yet another object of the present invention is to pass a length of suture material through anatomical tissue at an optimal distance from an opening formed in the anatomical tissue to receive a portal sleeve, thereby optimizing the quality of a closure formed with the suture material.

A still further object of the present invention is to optimally place a suture in anatomical tissue a predetermined distance from an opening formed in the anatomical tissue to receive a portal sleeve, the predetermined distance being optimally selected for the particular tissue thickness.

An additional object of the present invention is to facilitate placement of a suture a desired depth in anatomical tissue at a puncture site or opening whereby the suture is used to close the puncture site or opening.

It is also an object of the present invention to facilitate placement of a suture in selected layers of anatomical tissue at a puncture site or opening whereby the suture is used to close the selected layers, thereby closing the puncture site or opening.

Some of the advantages of the present invention are that puncture site closure in minimally invasive procedures is greatly simplified, the amount of time required for puncture site closure is greatly reduced, trauma to the patient associated with puncture site closure is reduced, the apparatus, kit and methods of the present invention are adaptable for use in closing puncture sites in anatomical tissue of varying thicknesses, the need to retract a large amount of tissue at a puncture site or opening during closure of one or more inner layers of the tissue at the puncture site or opening is reduced or eliminated, the extent to which a puncture site or opening needs to be stretched or enlarged during closure of the puncture site or opening is reduced or eliminated, the risk of needle damage and/or loss is reduced, the apparatus of the present invention can easily be modified to provide suture stitches of various sizes, a plurality of apparatus can be provided with each apparatus providing a different size suture stitch, an apparatus providing a particular suture stitch size can be optimally selected for use in a particular patient in accordance with the thickness of the anatomical tissue at the puncture site or opening, the apparatus can be designed for use with portal sleeves of various sizes, the apparatus can be supplied to surgeons as a kit including the apparatus and a penetrating instrument comprising a portal sleeve and an obturator used to form a puncture site or opening, a single apparatus can be used with more than one size portal sleeve, a plurality of different size apparatus can be provided with each apparatus being adapted for use with a specific size or sizes of portal sleeves, herniation, internal organ obstruction or strangulation, internal bleeding and/or fluid migration is/are avoided, the safety associated with use of larger size portal sleeves is enhanced, injury to internal organs or other anatomical structure is reduced since the penetrating member or needle can be inserted through the apparatus to be disposed only a minimal distance internally of the tissue being sutured, the suture stitches can be secured or tightened with a desired tension or strength, the apparatus, kit and methods of the present invention can be used in conjunction with conventional penetrating members or needles, conventional suture materials and/or conventional grasping instruments commonly available in operating rooms, and the apparatus of the present invention can be sterilizable for multiple uses or can be disposable for single patient use.

These and other objects, advantages and benefits are realized with the present invention as generally characterized in a puncture site closure apparatus for use in closing a puncture site or opening formed in anatomical tissue and through which a portal sleeve extends. The puncture site closure apparatus includes a collar for being disposed on the portal sleeve and having a central longitudinal axis and a cavity for receiving the portal sleeve such that the portal sleeve extends longitudinally through the collar. The puncture site closure apparatus further includes a pair of guide members disposed on opposite sides of the collar. Each of the guide members has a central longitudinal axis, upper and lower open ends and a lumen extending longitudinally therethrough. The collar is longitudinally movable relative to and along the portal sleeve to move the lower open ends of the guide members into the puncture site or opening to be disposed adjacent a selected layer of the anatomical tissue. The lumens of the guide members are adapted to receive a hollow penetrating member or needle therethrough whereby the penetrating member is guided by the guide member into and through the selected tissue layer as well as underlying layers of the anatomical tissue. The penetrating member enters and penetrates the anatomical tissue at an entry point and exits the anatomical tissue at an exit point such that an open distal end of the penetrating member is disposed internally of the tissue while an open proximal end of the penetrating member is disposed externally of the tissue. With the penetrating member extending through the tissue, a length of filamentous suture material can be passed therethrough such that a first end of the length of suture material protrudes from the open distal end of the penetrating member to be disposed internally of the tissue while a second end of the length of suture material protrudes from the open proximal end of the penetrating member to be disposed externally of the tissue. Accordingly, first and second lengths of suture material can be passed through the tissue via one or more penetrating members, as guided by the guide members, respectively. Upon withdrawal of the one or more penetrating members from the tissue, the first and second lengths of suture material remain in place in the tissue. The first and second lengths of suture material are then ready to be used to form a suture stitch or closure for closing the puncture site or opening upon removal of the portal sleeve.

In a preferred embodiment for the puncture site closure apparatus, the central longitudinal axes of the guide members define a predetermined angle with the central longitudinal axis of the collar, the guide members being angled in opposite directions from one another. The predetermined angle determines the radial distance between the entry points and a central longitudinal axis of the portal sleeve and, therefore, the center of the puncture site or opening. The predetermined angle thusly determines the size of the suture stitch or closure that will be formed with the first and second lengths of suture material and dictates the amount of tissue disposed between ends of the suture stitch or closure. By varying the predetermined angle of the guide members, the radial distance between the entry points and the central longitudinal axis of the portal sleeve can be varied in accordance with the thickness of the anatomical tissue being sutured so that the first and second lengths of suture material enter the tissue an optimal distance from the opening. In this manner, a puncture site closure apparatus can be optimally selected for use in a particular patient to obtain an optimal suture stitch size.

A kit for closing puncture sites or openings in anatomical tissue is generally characterized by a puncture site closure apparatus and a penetrating instrument used to form a puncture site or opening. The penetrating instrument includes a portal sleeve and an obturator or trocar for being disposed in the portal sleeve. The obturator has a distal end for penetrating anatomical tissue in order to position a distal end of the portal sleeve internally of the tissue, the portal sleeve thusly extending through a puncture site or opening formed in the tissue by the penetrating instrument. The obturator is removable from the portal sleeve, leaving the portal sleeve in place to establish communication with an internal operative site from externally of the tissue. The puncture site closure apparatus includes a collar adapted to be disposed on the portal sleeve and a pair of guide members carried by the collar. The collar is movable relative to and along the portal sleeve, while the portal sleeve extends through the opening, to position lower ends of the guide members adjacent a selected layer of the anatomical tissue. The guide members have lumens, respectively, therethrough for receiving a hollow penetrating member to guide the penetrating member through the tissue so that a length of suture material can be passed therethrough. The lower ends of the guide members correspond to entry points for the penetrating member and, therefore, the suture material, in the selected layer of the tissue. The guide members can be disposed on the collar at various angles to place first and second lengths of suture material in the tissue an optimal distance from the opening. The first and second lengths of suture material remain in the tissue for use in forming a suture stitch or closure following removal of the penetrating member or members from the guide members.

A method of closing a puncture site or opening in anatomical tissue through which a portal sleeve extends generally comprises the steps of positioning a collar of a puncture site closure apparatus on the portal sleeve while the portal sleeve is disposed in the opening, moving open lower ends of guide members, carried by the collar, into the opening to a desired depth, inserting a hollow penetrating member into a lumen of one of the guide members, advancing the penetrating member through the lumen of the one guide member to penetrate the anatomical tissue at an entry point on the anatomical tissue, moving the penetrating member through the tissue, as guided by the one guide member, to cause the open distal end of the penetrating member to exit the tissue at an exit point, passing a length of filamentous suture material through the penetrating member so that a first end of the length of suture material protrudes internally of the tissue through the open distal end of the penetrating member and a second end of the length of suture material is disposed externally of the tissue, introducing a grasping instrument through the portal sleeve, grasping the length of suture material internally of the tissue with a distal end of the grasping instrument, removing the penetrating member from the tissue, withdrawing the grasping instrument from the portal sleeve so that the first end of the length of suture material is drawn through the portal sleeve to be disposed externally of the tissue, repeating the inserting, advancing, moving passing, introducing, grasping, removing and withdrawing steps on the other guide member to place another length of suture material in the tissue, tying the first ends of the lengths of suture material together externally of the tissue to form a knot, passing the knot through the portal sleeve to dispose the knot internally of the tissue, withdrawing the portal sleeve from the opening and tying the second ends of the lengths of suture material together externally of the tissue to approximate the anatomical tissue at the opening and form a knot whereby a suture stitch or closure of desired strength or tension is formed in the tissue with the lengths of suture material. In exemplary embodiments, the tissue being sutured or closed includes abdominal and thoracic cavity walls.

Other objects and advantages of the present invention will become apparent from the following description of the preferred embodiments taken in conjunction with the accompanying drawings wherein like parts in each of the several figures are identified by the same reference characters.

BRIEF DESCRIPTION OF THE DRAWINGS

FIG. 3 is a broken side view, partly in section, showing the puncture site closure apparatus assembled on a portal sleeve of a penetrating instrument used to form a puncture site or opening in anatomical tissue through which the portal sleeve extends.

FIG. 4 is a broken side view, partly in section, illustrating guide members of the puncture site closure apparatus moved into the puncture site or opening with a hollow penetrating member inserted through one of the guide members to pass through selected layers of the anatomical tissue and showing a first length of filamentous suture material extending through the penetrating member and a grasping instrument grasping the first length of suture material internally of the tissue.

FIG. 5 is a broken side view, partly in section, illustrating the penetrating member inserted through the other guide member to pass through the selected tissue layers and showing a second length of filamentous suture material extending through the penetrating member and the grasping instrument grasping the second length of suture material internally of the tissue.

FIG. 6 is a broken side view, partly in section, depicting first ends of the first and second lengths of suture material, respectively, tied to one another externally of the anatomical tissue to form a knot.

FIG. 7 is a broken side view, partly in section, illustrating disposition of the knot internally of the anatomical tissue.

FIG. 8 is a broken side view, partly in section, illustrating withdrawal of the portal sleeve from the puncture site or opening and tying of second ends of the first and second lengths of suture material, respectively, with a desired tension to approximate the selected layers of the anatomical tissue at the puncture site or opening and form a knot, thusly forming a suture stitch or closure.

FIG. 11 is a top view of an alternative puncture site closure apparatus.

FIG. 12 is a broken side view, partly in section, illustrating formation of a suture stitch or closure in the thoracic cavity wall.

DESCRIPTION OF THE PREFERRED EMBODIMENTS

Figure 2:
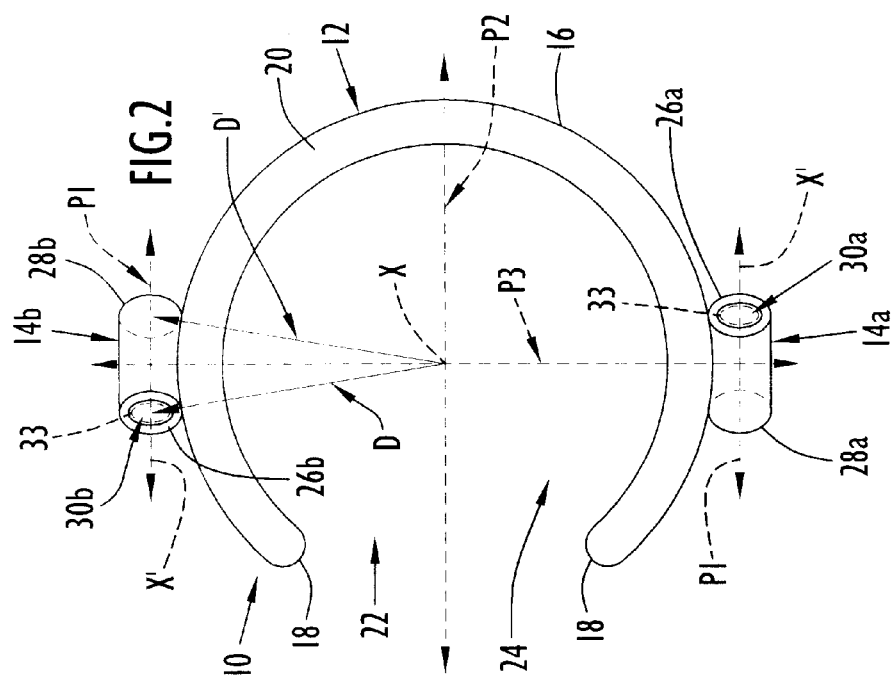
FIG. 2 is a top view of the puncture site closure apparatus.
Figure 1:
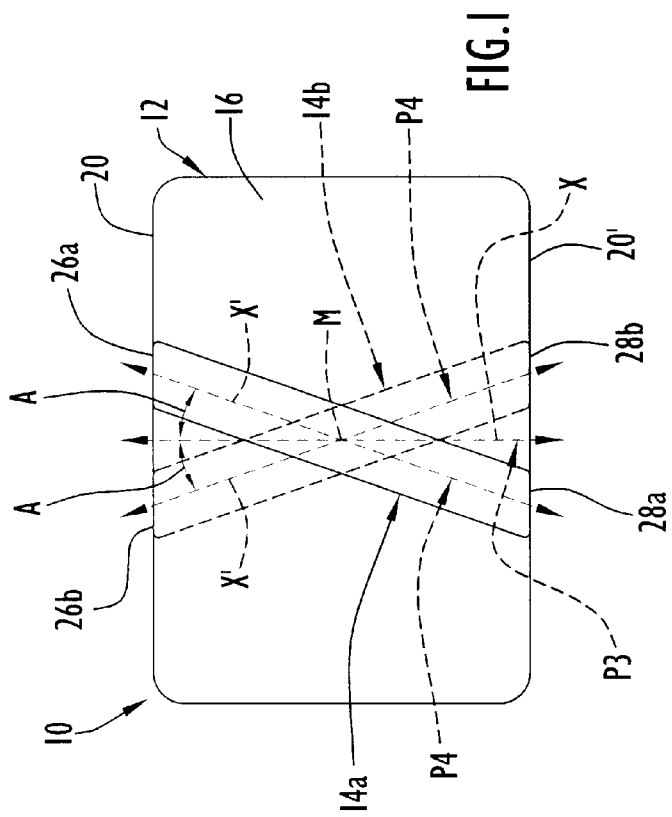
FIG. 1 is a side view of a puncture site closure apparatus according to the present invention.

A puncture site closure apparatus 10 according to the present invention is illustrated in FIGS. 1 and 2 and includes a collar 12 and a pair of guide members 14a and 14b disposed on the collar 12. Collar 12 includes a split ring or split cylinder having a wall 16 of uniform or substantially uniform thickness defining a partial circular or partial circumferential configuration about a central longitudinal axis X of collar 12. The wall 16 extends circumferentially between lateral edges 18 and extends longitudinally between opposite end edges or surfaces 20 and 20'. The end edges 20 and 20' are disposed in planes, respectively, parallel to one another and transverse or perpendicular to the central longitudinal axis X. Lateral edges 18 are parallel to central longitudinal axis X and are spaced from one another by a gap or slot 22 having a gap or slot width extending between the lateral edges 18, which constitute gap or slot edges. The gap 22 communicates with a cavity or passage 24 circumscribed by wall 16, and the gap 22 and cavity 24 extend the entire length of wall 16, which corresponds to the length of collar 12. Preferably, the lateral edges 18 and the end edges 20 and 20' are rounded, beveled or angled or otherwise blunt.

The collar 12 is normally in a non-expanded or relaxed position, shown in FIGS. I and 2, wherein the cavity 24 has an initial diametric or cross-sectional cavity size and the gap 22 has an initial gap width smaller than the initial cavity size. The initial cavity size is preferably slightly smaller than an external diametric or cross-sectional size of a portal sleeve S upon which the collar 12 is to be disposed as shown in FIG. 3 and as explained further below. The collar 12 is capable of being moved from the non-expanded position to an expanded position wherein the diametric or cross-sectional cavity size is increased from the initial cavity size to a second, larger cavity size, and the width of gap 22 is increased from the initial gap width to a second, larger gap width to allow the portal sleeve S to be passed through gap 22 into cavity 24 so that the portal sleeve S extends longitudinally through the collar 12 as shown in FIG. 3. The collar 12 is capable of being moved from the expanded position to or toward the non-expanded position subsequent to positioning of portal sleeve S in cavity 24, causing the portal sleeve S to be compressively and/or frictionally engaged or gripped by the collar 12. The compressive and/or frictional force or forces with which the collar 12 engages or grips the portal sleeve S is/are sufficient to prevent longitudinal and rotational movements of the collar 12 relative to the portal sleeve S in absence of a moving force or forces applied to collar 12, while permitting the collar 12 to be moved longitudinally and/or rotationally relative to the portal sleeve S when a longitudinal and/or rotational moving force or forces, sufficient to overcome the compressive and/or frictional force or forces, is/are applied to collar 12.

The collar 12 can be designed in various ways to be normally disposed in the non-expanded position, to be movable from the non-expanded position to the expanded position and to be movable from the expanded position to or toward the non-expanded position. For example, the collar 12 can be made of flexible, resilient, bendable or malleable materials allowing the collar 12 to flex, bend or deform to obtain the expanded position when an opening force is applied or exerted on collar 12 and to obtain the non-expanded position when a closing force is applied or exerted on collar 12. Preferably, the collar 12 is biased to the non-expanded position with the force of such bias providing the closing force for collar 12 such that the collar 12 is automatically moved from the expanded position to or toward the non-expanded position when the opening force on collar 12 is removed. The collar 12 can be biased to the non-expanded position in various ways including the use of one or more external and/or internal bias members such as springs and/or by virtue of the material or materials of which the collar 12 is made. In a preferred embodiment, the collar 12 is made of flexible or resilient material or materials, or material or materials having shape memory, with the collar 12 being biased to the non-expanded position by the flexibility or shape memory characteristics of the material or materials of which the collar 12 is made. In the preferred embodiment, collar 12 is made of spring or spring-like material, such as stainless steel.

The extent to which the initial gap width and the initial cavity size may be increased when the collar 12 is moved from the non-expanded position to the expanded position depends on the flexibility, resiliency, deformability or malleability of the collar 12 and also on the strength of the opening force applied or exerted on the collar 12 to move the collar 12 from the non-expanded position to the expanded position. Depending on the flexibility, resiliency, deformability or malleability of the collar 12, a single collar 12 can be provided to receive portal sleeves of different external diametric or cross-sectional sizes while establishing a compressive and/or friction fit with such portal sleeves and while permitting longitudinal and/or rotational movements of the collar relative to such portal sleeves in response to a moving force or forces, sufficient to overcome the compressive and/or frictional force or forces, applied to collar 12. It should be appreciated, therefore, that a single collar 12 can be identified or labeled for use with a plurality of portal sleeves of different sizes or for use with portal sleeves within an identified range of sizes. A plurality of collars 12 of different sizes and/or having different compressive and/or frictional gripping or engaging strengths can be provided, with each collar 12 being identified or labeled for use with a single, particular size portal sleeve.

The opening force used to move the collar 12 from the non-expanded position to the expanded position is typically in the form of a manual opening force produced by manual manipulation of the collar 12 by a surgeon or other medical personnel. Once the collar 12 is positioned or "snapped" onto the portal sleeve S, the collar 12 will remain in at least a slightly expanded position due to the presence of the portal sleeve S in the cavity 24. The portal sleeve S thusly provides an opening force maintaining the collar 12 in at least a slightly expanded position. The force or forces used to move the collar 12 longitudinally and/or rotationally relative to the portal sleeve S is/are typically a manual longitudinal and/or rotational force or forces in the form of manual manipulation of the collar 12 by the surgeon or other medical personnel.

Guide members 14a and 14b are externally disposed on collar 12 at diametrically opposite locations thereon. Guide members 14a and 14b include elongate, hollow cylindrical or tubular members, respectively, having open first ends 26a and 26b, respectively, and open second ends 28a and 28b, respectively, communicating with internal lumens 30a and 30b, respectively. The first ends 26a and 26b are defined by end edges or surfaces, respectively, that are contained in the plane of a first end surface or edge 20 of collar 12. The second ends 28a and 28b are similarly defined by end edges or surfaces, respectively, that are contained in the plane of a second end surface or edge 20' of collar 12. It should be appreciated, however, that the end edges of first ends 26a and 26b can extend longitudinally beyond the plane of the first end surface 20 and that the end edges of second ends 28a and 28b can extend longitudinally beyond the plane of the second end surface 20'. The guide members 14a and 14b have central longitudinal axes X', respectively, that are non-parallel with the central longitudinal axis X of collar 12; and, accordingly, the guide members 14a and 14b are angled relative to the central longitudinal axis X. As shown in FIG. 1, the central longitudinal axes X' are disposed at predetermined angle A to the central longitudinal axis X. The guide members 14a and 14b are disposed at the same angle A relative to the central longitudinal axis X but are angled in directions opposite to one another.

The central longitudinal axes X' are disposed in first planes P1, respectively, that are parallel to one another and to a plane P2 containing the central longitudinal axis X as shown in FIG. 2. The central longitudinal axes X' are also contained in planes P4, respectively, transverse to planes P1 and disposed at angle A to a plane P3 as shown in FIG. 1. The plane P3 contains the central longitudinal axis X and is perpendicular to and intersects plane P2, also containing the central longitudinal axis X. Planes P4 intersect or cross one another at a location M centrally located between the planes of end edges 20 and 20', and plane P3 intersects planes P4 at location M. Plane P4 of guide member 14a defines angle A with plane P3 above and below location M, plane P4 of guide member 14a defining angle A on a first side of plane P3 above location M and defining angle A on a second or opposite side of plane P3 below location M. Plane P4 of guide member 14b also defines angle A with plane P3 above and below location M, plane P4 of guide member 14b defining angle A on the second side of plane P3 above location M and defining angle A on the first side of plane P3 below location M. Accordingly, guide member 14a is angled in a first direction relative to plane P3 and, therefore, central longitudinal axis X, while guide member 14b is angled in a second, opposite direction relative to plane P3 and axis X. Thus, an angle equivalent to two times A is defined between planes P4 both above and below location M.

The guide members 14a and 14b are spaced 180° from one another to be disposed at diametrically opposite locations on collar 12. However, it should be appreciated that the guide members 14a and 14b can be disposed at various locations on collar 12 and that the guide members do not have to be spaced 180° from one another depending on procedural use. The first ends 26a and 26b are disposed at diametrically opposite locations along the first end surface 20, and the second ends 28a and 28b are disposed at diametrically opposite locations along the second end surface 20'. Because of the angle A of the guide members, the first end 26a is not vertically aligned with but, rather, is vertically offset from the second end 28a. Similarly, the first end 26b is not vertically aligned with but, rather, is vertically offset from the second end 28b. The ends 26a, 26b, 28a and 28b are preferably rounded, angled, beveled or otherwise blunt to avoid injury or harm to anatomical tissue. A preferred material for guide members 14a and 14b is stainless steel in order to avoid gouging or scratching of the guide members by a penetrating member inserted therein as explained further below.

The predetermined angle A determines the radial distance D between the first ends 26a and 26b and the longitudinal axis X and the radial distance D' between the second ends 28a and 28b and the longitudinal axis X, the distances D and D' being shown in FIG. 2 for guide member 14b. In particular, angle A determines the radial distance D between axis X and axes X' in the plane of the first ends 26a and 26b and the radial distance D' between axis X and axes X' in the plane of the second ends 28a and 28b. In the case of puncture site closure apparatus 10, radial distance D is equal to or the same as radial distance D' as shown in FIG. 2. By varying angle A for the guide members, the radial distances D and D' can also be varied. For instance, larger radial distances D and D' can be obtained by increasing the size of angle A while smaller radial distances D and D' can be obtained by decreasing the size of angle A. In this manner, a particular angle A can be selected for the guide members in order to obtain a particular predetermined radial distance to form a desired size suture stitch or closure in anatomical tissue of a specific patient in accordance with the thickness of the tissue as explained further below.

In one embodiment for puncture site closure apparatus 10, the collar 12 and the guide members 14a and 14b are made of stainless steel with the guide members 14a and 14b welded to the collar 12. Preferably, weld seams are burnished to obtain a flat or smooth finish. In another embodiment, which is preferred for its lower cost, simplicity and efficiency of manufacture, the collar and guide members are integrally, unitarily molded of plastic with the guide members having stainless steel linings, respectively, to prevent gouging of the plastic by the needles. FIG. 2 illustrates in dotted lines exemplary steel linings 33 in guide members 14a and 14b, respectively. The width of gap 22 in the non-expanded position can vary. The lateral edges 18 can touch or be adjacent one another or can be spaced various distances from one another in the non-expanded position. Material costs can be reduced by providing the collar with an initial gap width as large as possible while providing sufficient compressive and/or frictional gripping force on the portal sleeve and sufficient support for the guide members and the penetrating member or members to be received therein as explained further below. The length of the collar can vary and can be minimized to reduce material costs while maintaining sufficient support for the guide members and the penetrating member or members to be received therein, sleeve 11 mm or greater in size, and the lumens 30a and 30b have a diameter to receive a 17 gauge hollow Touhy needle therein with a friction fit as described further below. A preferred angle A for the guide members is in the range of 3 to 20 degrees. Of course, the particular structural dimensions of the puncture site closure apparatus 10 can be modified in accordance with the size of the portal sleeve and/or the size of the penetrating member or members to be used therewith and/or the dimensions of the tissue to be repaired. The puncture site closure apparatus 10 can be reusable or can be disposable for single patient use. Where the puncture site closure apparatus 10 is made of stainless steel, for example, the apparatus 10 can be sterilized, such as by heat autoclaving or chemical sterilization, for repeated use.

According to a method of puncture site closure in accordance with the present invention, the puncture site closure apparatus 10 is used in combination with a portal sleeve disposed within a puncture site or opening created in anatomical tissue of a patient in order to provide access through the tissue to an internal operative site. As shown in FIG. 3, the portal sleeve S is disposed within a puncture site or opening O formed in anatomical tissue T of a patient such that a lumen 31 through the portal sleeve S provides a passage or portal through the tissue T establishing communication with an internal operative site from externally of the tissue T, typically from externally of the patient's body. In the illustrated method, the tissue T is an anatomical cavity wall W and, in particular, the abdominal cavity wall W. The portal sleeve S extends entirely through cavity wall W to communicate with an anatomical cavity C which, in the illustrated method, is the abdominal cavity C. The cavity wall W has a depth or thickness t formed by a plurality of tissue layers. In the illustrated method, the cavity wall W includes an external tissue layer 32, an intermediate tissue layer 34 and an inner tissue layer 36. The external tissue layer 32 may itself comprise one or more tissue layers; and, in the case of the abdominal cavity wall, the external tissue layer is comprised of skin 32. The intermediate tissue layer 34 may itself comprise one or more tissue layers; and, in the case of the abdominal cavity wall, the intermediate tissue layer is comprised of subcutaneous tissue or fat 34, the tissue layers 32 and 34 comprising superficial or outer tissue layers. The inner tissue layer 36 may itself also comprise one or more tissue layers; and, in the case of the abdominal cavity wall, the inner tissue layer 36 includes the internal investing fascia 35, the wall musculature 37 including layers of muscle, and the peritoneum 38, which is the innermost tissue layer of the abdominal cavity wall. The puncture site closure apparatus 10 enables suturing of selected tissue layers beginning at a desired or selected depth within the tissue T.

The portal sleeve S passes through the thickness t of tissue T to be disposed within the cavity C. In the illustrated procedure, the portal sleeve S passes through skin 32, subcutaneous tissue or fat 34, internal investing fascia 35, musculature 37 and peritoneum 38 such that a distal end 40 of the portal sleeve S passes through the peritoneum 38 to be disposed within the abdominal cavity C, which contains an internal operative site. The portal sleeve S is positioned in the puncture site or opening O with the use of an obturator P, such as a trocar, removably received in the lumen 31 of the portal sleeve S. The portal sleeve S and the obturator P form part of a penetrating instrument conventionally used in minimally invasive procedures to form a puncture site or opening in anatomical tissue and place the portal sleeve within this opening. Exemplary penetrating instruments include the Endopath of Ethicon Endo-Surgery and the SurgiPort of U.S. Surgical Corporation. The puncture site closure apparatus 10 can be supplied to surgeons, hospitals and the like as part of a kit comprising the penetrating instrument and the puncture site closure apparatus. The obturator P has a distal end or tip 37 for penetrating tissue T. When the obturator is disposed in the portal sleeve, the tip 37 protrudes distally beyond the distal end 40 of the portal sleeve.

The obturator P is used to penetrate the wall W to pass the portal sleeve S therethrough; and, upon the distal end 40 of the portal sleeve passing internally through the tissue T, the obturator is withdrawn from the portal sleeve as shown in FIG. 3, leaving the portal sleeve to extend through the opening O. In the case of abdominal cavity wall W, the obturator and portal sleeve may be inserted through the wall W subsequent to gaseous insufflation of the abdominal cavity C to create a pneumoperitoneum. However, it should be appreciated that the portal sleeve can be introduced through the cavity wall prior to creation of a pneumoperitoneum as would be the case in "open laparoscopy", for example, where the obturator and portal sleeve are introduced through an initial small incision, typically formed in the abdominal cavity wall with a Veress needle, prior to insufflation of the abdominal cavity. Upon creation of a pneumoperitoneum, the abdominal cavity C is distended or expanded to separate wall W from internal organs or other anatomical structures and create increased space within cavity C. The opening O has a diametric or cross-sectional size the same as or substantially the same as the external diametric or cross-sectional size of the portal sleeve S. Upon conclusion of an operative procedure performed in the cavity C with one or more instruments introduced at the operative site through the lumen 31 of the portal sleeve S, the puncture site or opening O should or must be repaired or closed in order to avoid post-operative complications.

In order to close the puncture site or opening O in accordance with the present invention, a puncture site closure apparatus 10 is selected in accordance with the external diametric or cross-sectional size of the portal sleeve S and the desired size of a suture stitch or closure to be formed in tissue T. When supplied as part of a kit, the puncture site closure apparatus will be pre-selected for use with the portal sleeve of the penetrating instrument with which it is supplied. Where the portal sleeve S is an 11 mm portal sleeve, for example, an apparatus 10 is selected with a collar 12 having a cavity 24 capable of receiving or accommodating the portal sleeve S therein with a compressive and/or friction fit as described above. Of course, the portal sleeve S can be of any diameter and length. The apparatus 10 selected for the particular patient will have a predetermined angle A so that lengths of filamentous suture material passed through the guide members, respectively, enter the anatomical tissue T at entry points located a desired radial distance from the central longitudinal axis X and, therefore, a desired distance from a central longitudinal axis of portal sleeve S and the center of the puncture site or opening O, in accordance with the thickness of tissue T as explained further below.

Once a puncture site closure apparatus 10 has optimally been selected for the particular portal sleeve S and the particular tissue thickness, the collar 12 of the selected apparatus 10 is manually moved from the non-expanded position to the expanded position to permit the portal sleeve S to pass through the gap 22 into the cavity 24. The collar 12 can be manually flexed or expanded, such as by the hand or hands of the surgeon or other medical personnel, to increase the initial gap width, or the collar 12 can be manually pressed against the portal sleeve S with the portal sleeve S in alignment with the gap 22. In the former case, the opening force on collar 12 is due to direct manual expansion of the collar 12 by the surgeon or other medical personnel. In the latter case, the opening force is due to the portal sleeve S being forced through the gap 22 into the cavity 24. In either case, the collar 12 is positioned or "snapped" onto the portal sleeve S by moving the collar 12 from the non-expanded position to the expanded position in response to an opening force applied thereto to cause the portal sleeve S to be received within the cavity 24 with the portal sleeve S extending longitudinally through the collar 12 as shown in FIG. 3.

Once the portal sleeve S is received within the cavity 24, the manual opening force applied to the collar 12 in order to position the portal sleeve S in the cavity 24 is removed. The collar 12 moves or is moved toward the non-expanded position, causing the portal sleeve S to be compressively and/or frictionally gripped, engaged or grasped by the collar 12. Since the initial cavity size of the collar 12 is typically slightly smaller than the external diametric or cross-sectional size of the portal sleeve S, the collar 12 will typically remain in a slightly expanded position due to the opening force provided by the presence of the portal sleeve S within the cavity 24 and will thusly compressively and frictionally grip or engage the portal sleeve S due to the bias of the collar 12 toward the non-expanded position. Where a kit is provided, the puncture site closure apparatus may be preassembled on the portal sleeve if desired to eliminate the foregoing step during surgery.

Once the collar 12 is disposed upon the portal sleeve S as shown in FIG. 3, the collar 12 is manually moved longitudinally relative to and along the portal sleeve S in order to position open second ends 28a and 28b of the guide members 14a and 14b, respectively, at a desired depth within the puncture site or opening O, the open second ends 28a and 28b defining lower open ends of the guide members. In particular, the collar 12 is moved longitudinally in the direction of the anatomical cavity wall W, and the skin 32 will typically be retracted a small amount adjacent the puncture site or opening O to allow the lower open ends 28a and 28b of the guide members 14a and 14b, respectively, to be moved into the puncture site or opening O. Depending on the dimension of the original incision through the skin, this may require small extrusion of the original incision to accommodate the additional dimension of apparatus 10. As shown in FIG. 4, the open second ends 28a and 28b of guide members 14a and 14b, respectively, are moved into the puncture site or opening O a desired or selected depth and are disposed near adjacent or in abutment with a selected layer of tissue T. In the illustrated procedure, the second ends 28a and 28b are disposed near the internal investing fascia 35. As shown in FIG. 4, the lower ends 28a and 28b are positioned in contact with the subcutaneous tissue 34 just above the internal investing fascia 35 with a small or minimal depth or thickness portion of subcutaneous tissue 34 between the lower ends 28a and 28b and the internal investing fascia 35.

Once the puncture site closure apparatus 10 has been moved into the puncture site or opening O to a selected or desired depth, a hollow or cannulated penetrating member such as a needle 44 is introduced into one of the guide members and is inserted through the depth or thickness portion of intermediate tissue layer 34 and through the inner tissue layer 36 of anatomical tissue T while the pneumoperitoneum is maintained in the cavity C. This may be done under direct observation by the surgeon by placement of an endoscope or laparoscope in an observational position via a second, independent portal sleeve usually in place for this purpose at a second site, for example the umbilicus or some other site. The needle 44 includes an open, tissue penetrating distal end or tip 45, an open proximal end 46 and a lumen therethrough. The needle 44 has an external diametric or cross-sectional size the same as or substantially the same as the diametric or cross-sectional size of lumens 30a and 30b to be concentrically received therein with a friction fit while allowing the needle 44 to be moved longitudinally distally and proximally relative to the guide members 14a and 14b. As shown in FIG. 4, the needle 44 is inserted, tip first, into and through the lumen 30a of guide member 14a, the needle 44 entering the guide member 14a via the open first end 26a, which defines an open upper end for the guide member 14a. The needle 44 is shown inserted through the depth or thickness portion of subcutaneous tissue or fat 34, the internal investing fascia 35, the muscle layer 37 and the peritoneum 38 so that the tip 45 of the needle 44 has passed through the peritoneum 38 and entered the abdominal cavity C while the proximal end 46 of the needle 44 remains external of the cavity wall W, typically external of the patient's body. As it is inserted through the anatomical cavity wall W, the needle 44 is guided by the guide member 14a and thusly follows or continues the angle A of the guide member 14a as it passes through the cavity wall W. Accordingly, the needle 44 extends through the depth or thickness portion of intermediate tissue layer 34 and through the inner tissue layer 36 at angle A relative to the central longitudinal axis X, the central longitudinal axis of portal sleeve S and the center of opening O.

The needle 44 penetrates the depth or thickness portion of intermediate tissue layer 34 at an entry point 42 on the tissue layer 34, passes through the depth or thickness portion, the internal investing fascia 35, muscle layer 37 and peritoneum 38 to exit the peritoneum 38 at an exit point 48 on the tissue layer 36. The entry and exit points of the needle 44 are both disposed in the first plane P1 of the guide member 14a. In addition, the entry point 42 is disposed the predetermined radial distance D' from the central longitudinal axis X, the central longitudinal axis of portal sleeve S and the center of opening O. Accordingly, a predictable or predetermined amount of tissue T is disposed between the entry point 42 and the central longitudinal axis of portal sleeve S and the center of the opening O. Due to the angle of needle 44, as determined by the angle A of guide member 14a, the exit point 48 will be disposed a radial distance, greater than radial distance D', from the central longitudinal axis X, the central longitudinal axis of portal sleeve S and the center of opening O. The exit point 48 will be spaced from the entry point 42, within the first plane P1 of guide member 14a, such that the entry point 42 will not be vertically aligned with but, rather, will be vertically offset from, the exit point 48 within plane P1. The entry point 42 is disposed the selected or desired depth within the tissue T, i.e. cavity wall W.

The needle 44 is illustrated in FIG. 4 as a 17 gauge Tuohy needle, which is characterized by a curving or spoon-shaped distal end or tip 45 which can be used to direct the suture medially to axis X. A Tuohy needle is preferred since it is conventionally available in operating rooms; however, it should be appreciated that other types of needles or hollow penetrating members may be used. As shown in FIG. 4, the tip 45 of the needle 44 may not need to extend very far internally of the anatomical tissue T. In FIG. 4, the open tip 45 of the needle 44 has cleared the internal surface of peritoneum 38 and protrudes into the abdominal cavity C only a small amount so that the risk of injury to internal organs or other anatomical structures from contact with the tip 45 is minimized. Of course, depending on the configuration of tip 45, the open tip 45 may be flush or aligned with the internal surface of cavity wall W without protrusion into the cavity C. The risk of injury to organs or other structure internal to wall W is also minimized by the maintenance of a pneumoperitoneum. The needle 44 will be maintained in a desired longitudinal position relative to the guide member 14a due to the friction fit of needle 44 with guide member 14a.

With the needle 44 extending through the depth or thickness portion of tissue layer 34 and through the entire thickness or depth of tissue layer 36, a first length of conventional, filamentous suture material 50 having first and second ends 52 and 54, respectively, is passed through the lumen of the needle 44 such that the first end 52 of the length of suture material 50 protrudes distally from the tip 45 and is disposed internally of the tissue T while the second end 54 of the length of suture material 50 protrudes or extends externally from the proximal end 46 to be disposed externally of the tissue T, typically external of the patient's body, as shown in FIG. 4. The length of suture material 50 is passed through the needle 44 from externally of cavity wall W, the length of suture material 50 entering the open proximal end 46 and exiting the open distal end or tip 45. The suture material 50 is illustrated as a monofilament suture material; however, the suture material 50 can be a multifilament suture material.

As shown in FIG. 4, a conventional grasping instrument 60 is introduced internally of the anatomical tissue T in order to grasp the length of suture material 50 and draw the first end 52 thereof outwardly through the portal sleeve S. The grasping instrument 60 shown in FIG. 4 has a distal end carrying or formed as a pair of pivotal grasping members 62 movable, via a handle (not shown) at a proximal end of the grasping instrument, between a closed or grasping position and an open or non-grasping position. When the grasping members 62 are in the open position, a portion of the first length of suture material 50 can be received therebetween. When the grasping members 62 are thereafter moved to the closed position, the portion of the length of suture material 50 is grasped and held between the grasping members 62.

The grasping instrument 60 is introduced through the lumen 31 of portal sleeve S to position the grasping members 62 internally of the tissue T and, in the case of cavity wall W, within the anatomical cavity C. The grasping members 62 are operated to grasp the first length of suture material 50 internally of tissue T. In particular, the grasping instrument 60 is manipulated via the handle at the proximal end thereof, which is disposed externally of the patient's body, in order to place a portion or portions of the first length of suture material 50 between the grasping members 62 with the grasping members 62 in the open position. The grasping members 62 are thereafter moved, via actuation of the handle at the proximal end of the grasping instrument, to the closed position in order to grasp the portion or portions of the first length of suture material 50 therebetween as shown in FIG. 4. Once the first length of suture material 50 is grasped by the grasping members 62, the needle 44 is manually removed or withdrawn from the guide member 14a and from the tissue T.

Upon removal or withdrawal of the needle 44 from the guide member 14a and the tissue T, as shown in FIG. 5, the first length of suture material 50 remains in the tissue T, the first length of suture material 50 entering the tissue T at the entry point 42 and exiting the tissue T at the exit point 48. Accordingly, the length of suture material 50 extends through a thickness portion of the tissue T between the entry point 42 and the exit point 48. Upon removal of needle 44, the grasping instrument 60 is manually withdrawn through the lumen 31 of the portal sleeve S causing the first end 52 of the first length of suture material 50 grasped thereby to be drawn outwardly through the lumen 31 along with the grasping instrument 60. Once the grasping instrument 60 is withdrawn from the portal sleeve S, the first end 52 of the first length of suture material 50 will extend proximally from the proximal end of the portal sleeve S as shown in FIG. 5. As shown in FIG. 5, the first and second ends 52 and 54 can be secured to one another, such as by a clamp 55, externally of the patient to facilitate procedural use.

Once the first end of the first length of suture material 50 has been drawn through the proximal end of the portal sleeve S, the same or a different penetrating member 44 is introduced through the other guide member 14b for insertion through the tissue T on the opposite side of the portal sleeve S in the same manner. Alternatively but less preferably, a second penetrating member or needle may be introduced through guide member 14b prior to withdrawal of needle 44 from the guide member 14a. However, it is preferable that only one needle at a time extend or protrude into the cavity C. As shown in FIG. 5, the needle 44 is introduced through the lumen 30b of guide member 14b and is inserted through the depth or thickness portion of intermediate tissue layer 34 and through the entire depth or thickness of inner tissue layer 36 in the same manner as described above for guide member 14a. The needle 44 is guided through the tissue T by the guide member 14b and thusly extends through the depth or thickness portion of tissue layer 34 and through the entire depth or thickness of tissue layer 36 at the angle A, opposite to the angle A of the guide member 14a. The needle 44 enters the depth or thickness portion of the subcutaneous tissue or fat 34 at entry point 42' and exits the peritoneum 38 at exit point 48', the open tip 45 of the needle 44 passing through the peritoneum 38 to be disposed slightly within the anatomical cavity C. The entry and exit points 42' and 48' are disposed in the first plane P1 of the guide member 14b, and the entry point 42' is disposed radial distance D' from axis X, the longitudinal axis of the portal sleeve S and the center of opening O. In this manner, a predictable or predetermined amount of tissue T is disposed between the entry point 42' and the central longitudinal axis of portal sleeve S and the center of opening O. The exit point 48' will be disposed a radial distance from the axis X, the central longitudinal axis of portal sleeve S and the center of opening O that is the same as the radial distance between the exit point 48 and the axis X, the central longitudinal axis of portal sleeve S and the center of opening O. The entry point 42' is spaced from the exit point 48', in the plane P1 of guide member 14b, such that the entry and exit points 42' and 48' are not vertically aligned but, rather, are vertically offset, within plane P1 of guide member 14b.

A second length of conventional filamentous suture material 50' having first and second ends 52' and 54', respectively, is passed through the lumen of needle 44 in the manner previously described for passage of the first length of suture material 50 through needle 44. The first end 52' of the second length of suture material 50' extends or protrudes distally from the tip 45, and is thusly disposed within the anatomical cavity C as shown in FIG. 5. The second end 54' of the second length of suture material 50' extends proximally from the proximal end 46 to be disposed externally of the tissue T and, therefore, externally of the patient's body.

As shown in FIG. 5, a remote viewing device such as an endoscope or laparoscope 56 may be introduced through the lumen 31 of the portal sleeve S to position an image receiving distal end 58 of the remote viewing device 56 internally of the anatomical tissue T. In this manner, penetration of the tip 45 of the needle 44 internally of the anatomical tissue T as well as passage of the first ends 52 and 52' of the first and second lengths of suture material 50 and 50', respectively, through the tip 45 can be visualized and thusly confirmed from externally of the patient's body as would be representative of a single puncture technique. The remote viewing device may be rigid or non-flexible, or the remote viewing device may be a flexible, bendable or directional scope wherein the angular orientation or position of image receiving end 58 can be selectively controlled or adjusted to facilitate visualization. It should be appreciated that the remote viewing device 56 does not have to be introduced through the portal sleeve S and that the remote viewing device 56 could be introduced internally of the tissue T through another artificially created or natural anatomical opening including another portal sleeve disposed within another puncture site or opening in the anatomical tissue as in the case of multiple puncture site procedures.

The grasping instrument 60 is introduced through the lumen 31 of portal sleeve S, and the distal end of the grasping instrument 60 is used to grasp a portion or portions of second length of suture material 50' internally of tissue T as shown in FIG. 5 and as described above for first length of suture material 50. Once the second length of suture material 50' is grasped by the grasping instrument, the needle 44 is removed from the guide member 14b and the tissue T, leaving the second length of suture material 50' within the tissue. As described above for the first length of suture material, the second length of suture material 50' enters the depth or thickness portion of intermediate tissue layer 34 at entry point 42' and exits the peritoneum 38 at exit point 48'. Upon removal of needle 44, the grasping instrument 60 is withdrawn from the portal sleeve S, thereby drawing the first end 52' outwardly or externally from the portal sleeve. Accordingly, the first and second ends 52' and 54' of the second length of suture material 50' will be disposed externally of tissue T and, along with the first and second ends 52 and 54 of the first length of suture material 50, will be accessible to the surgeon.

Since the lengths of suture material are drawn outwardly through the portal sleeve after the needle or needles has/have been removed, unintentional shearing of the lengths of suture material by the tip or tips of the needle or needles is avoided. In the illustrated procedure, the lengths of suture material are drawn through the portal sleeve individually, sequentially. It should be appreciated, however, that the lengths of suture material can be drawn through the portal sleeve simultaneously where the grasping instrument is designed for or otherwise capable of grasping the first and second lengths of suture material at the same time. The needle or needles can be withdrawn from the tissue while remaining within the guide members 14a and 14b, or the needle or needles can be withdrawn entirely from the guide members 14a and 14b. The needle or needles can remain within the guide members 14a and 14b and still be withdrawn from the tissue by withdrawing the needle or needles partially from the guide members 14a and 14b to exit the tissue externally, while the collar 12 remains on the portal sleeve S, or by moving the collar 12 longitudinally, proximally relative to and along the portal sleeve S so as to withdraw the needle or needles from the tissue without moving the needle or needles relative to the guide members. Also, the collar 12 can be removed from the portal sleeve S, with or without the needle or needles already withdrawn from the guide members, once the first ends of the first and second lengths of suture material have been disposed internally of tissue T and prior or subsequent to disposition of first ends 52 and 52' externally of the portal sleeve S. More typically, the puncture site closure apparatus will be removed after a knot has been formed in the first ends of the lengths of suture material and has been disposed internally of the tissue as explained further below. The needle or needles and/or the puncture site closure apparatus can be removed from the portal sleeve prior to removal of the portal sleeve from the opening, or the needle or needles and/or the puncture site closure apparatus can remain on the portal sleeve while the portal sleeve is withdrawn from the opening. It should be appreciated that the remote viewing device 56 can be used to visualize grasping of the lengths of suture material by the grasping instrument internally of the tissue T, and the image receiving distal end 58 of the remote viewing device 56 can be introduced internally of tissue T through the portal sleeve S or through another, different portal such as a second portal sleeve.

The first ends 52 and 52' of the first and second lengths of suture material 50 and 50', respectively, are tied together in a conventional manner externally of the tissue T and, typically, externally of the patient's body, to form knot 64 externally of the portal sleeve S as shown in FIG. 6. If necessary, the first ends 52 and 52' can be trimmed or cut to minimize the length of free end portions of the first ends 52 and 52', respectively, extending from the knot 64. Once the knot 64 has been formed, it is dropped through the lumen 31 and is thusly passed inwardly through the lumen 31 to be discharged from the distal end 40 of the portal sleeve S. Passage of the knot 64 through and from the portal sleeve S for disposition internally of the tissue T can be facilitated, if necessary, by pushing the knot 64 through the portal sleeve S with an appropriate instrument and/or by pulling outwardly on the second ends 54 and 54' of the first and second lengths of suture material 50 and 50'. Pulling outwardly on the second ends 54 and 54' is feasible since the needle or needles is/are removed and thusly does/do not present a risk of shearing the suture material. FIG. 7 illustrates the knot 64 discharged from the distal end 40 of the portal sleeve S into the anatomical cavity C.

Following disposition of knot 64 internally of the tissue T, the portal sleeve S, with or without the puncture site closure apparatus 10 already removed therefrom, is removed or withdrawn from the puncture site or opening O. Thereafter, the second ends 54 and 54' of the first and second lengths of suture material 50 and 50', respectively, are pulled with desired force in order to approximate the tissue edges 66 presented at the opening O upon removal of the portal sleeve S. As shown in FIG. 8, the second ends 54 and 54' are tied to one another externally of tissue T and, typically, externally of the patient's body, to form a knot 68 to complete a suture stitch or closure in tissue T, the first and second lengths of suture material 50 and 50' having been pulled to obtain a suture stitch or closure of desired strength or tension. The knot 68 is disposed externally of the depth or thickness portion of intermediate tissue layer 34 while the knot 64 is disposed interiorly or internally of the inner tissue layer 36 with the tissue edges 66 being approximated for healing. The second ends 54 and 54' of the first and second lengths of suture material 50 and 50' are cut or trimmed as necessary to minimize the length of free end portions of the first and second lengths of suture material extending from the knot 68, which is disposed within the intermediate tissue layer 34. The outer tissue layer or skin 32 and/or the remaining depth or thickness of tissue layer 34 is/are closed or repaired superficially by suturing in a conventional manner. If indicated or desired, the collar 12 can be manually rotated approximately 90° relative to the portal sleeve S, and the procedure can be repeated to place third and fourth lengths of suture material in the tissue. In this manner, the first and second lengths of suture material can be used to form a first suture stitch or closure while the third and fourth lengths of suture material can be used to form a second suture stitch or closure at the puncture site, the first and second suture stitches or closures crossing one another at the puncture site.

The suture stitch or closure formed in the tissue layers 34 and 36 with the first and second lengths of suture material 50 and 50' facilitates and insures proper healing or closure of the puncture site or opening O and prevents various post-operative complications such as excessive bleeding, herniation, strangulation of the bowel or other viscera and/or fluid migration into internal tissue layers. In particular, the suture stitch or closure formed in accordance with the present invention significantly reduces the risk of postoperative complications in minimally invasive procedures utilizing relatively large portal sleeves. The entry points for the suture material in the tissue are located a selected or desired depth within the tissue; and, accordingly, the suture stitch or closure begins at the selected or desired depth within the tissue. The suture stitch or closure is formed in a desired layer or layers of the tissue, the suture stitch beginning at a desired or selected tissue layer and extending through the desired or selected tissue layer as well as the tissue layer or layers underlying the desired or selected tissue layer. Penetration of the desired or selected tissue layer by the suture material at an optimal location is easily insured by positioning the lower ends of the guide members at the desired or selected tissue layer. The suture material is automatically passed through the desired or selected tissue layer or layers as well as the underlying tissue layer or layers at a favorable angle due to the angle of the guide members. The entry and exit points for the suture material in the tissue are located an optimal distance outwardly of the tissue edges to ensure a sufficient amount of tissue within the suture stitch or closure for the particular tissue thickness. Since the entry points are not vertically aligned with the corresponding exit points, the tissue is engaged by the suture material at two different locations on each side of the approximated tissue edges. In this manner, a single suture stitch or closure secures the tissue along a greater or increased portion of the length of the approximated tissue edges. Accordingly, even large size puncture sites or openings can be securely approximated with a single suture stitch or closure or, if necessary, multiple suture stitches or closures formed in the same manner.

Figure 9:
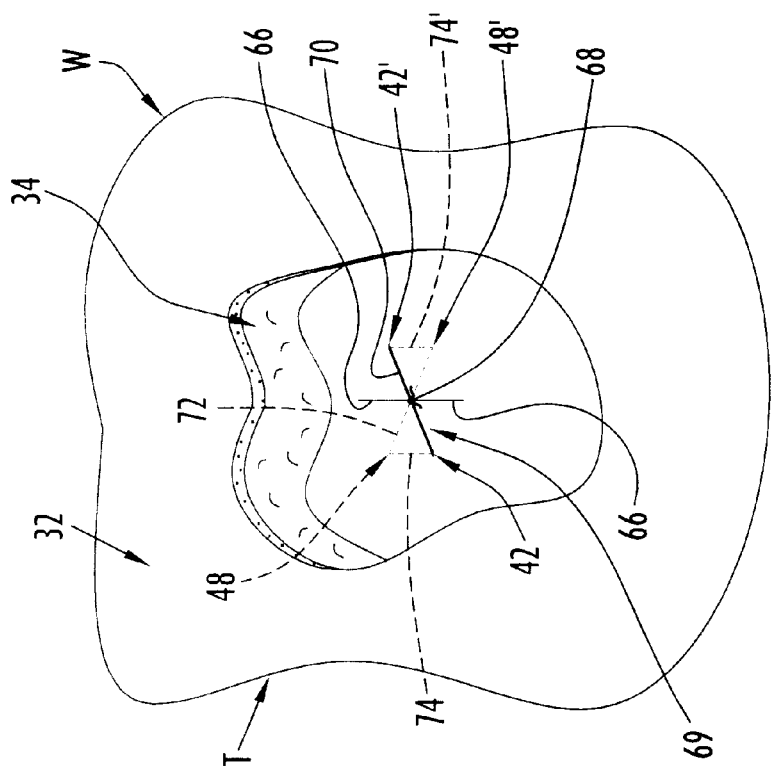
FIG. 9 is a broken top view illustrating the suture stitch or closure formed in the anatomical tissue with the first and second lengths of suture material.

FIG. 9 illustrates the suture stitch or closure 69 formed in accordance with the present invention, the length and width of the suture stitch or closure being exaggerated for the sake of clarity. Since the entry point 42 is vertically offset from and not aligned with the exit point 48 and since the entry point 42' is similarly vertically offset from or not aligned with the exit point 48', the suture stitch or closure 69 has a crisscross or X-shaped configuration including an external length portion 70 extending diagonally between the entry points 42 and 42' and an internal length portion 72 extending diagonally between the exit points 48 and 48'. The internal and external length portions 70 and 72 define a length for the suture stitch or closure. The suture stitch or closure also includes transverse portions 74 and 74' that extend through the tissue T. The transverse portion 74 extends angularly between the entry point 42 and the exit point 48 in a direction opposite the transverse portion 74', and the transverse portion 74' extends angularly between the entry point 42' and the exit point 48' in a direction opposite the transverse portion 74. The transverse portions 74 and 74' define a width for the suture stitch or closure.

In accordance with the present invention, the puncture site closure apparatus 10 can be easily modified to obtain suture stitches or closures of various sizes. The angle A of the guide members 14a and 14b determines the length and width of a suture stitch or closure to be obtained in accordance with the subject invention. Accordingly, the angle A of guide members 14a and 14b can be varied or changed in order to obtain a desired suture or closure stitch length and width for a given patient. For example, a relatively large angle A provides a greater radial distance D' and, therefore, a greater stitch or closure length. A relatively larger angle A also provides a greater spacing between the entry point and its corresponding exit point within the first plane of the corresponding guide member and, therefore, provides a suture stitch or closure of relatively larger width. A relatively smaller angle A for the guide members provides a smaller radial distance D' and, therefore, a suture stitch or closure of relatively smaller length. A relatively smaller angle A also provides a smaller spacing between the entry point and its corresponding exit point within the first plane of the corresponding guide member and thusly provides a suture stitch or closure of relatively smaller width. A relatively smaller angle A may be particularly advantageous for heavy or obese patients wherein the tissue being sutured is of relatively greater thickness, the relatively larger angle A possibly resulting in an excessive amount of tissue between ends of the suture stitch. A relatively larger angle A may be desirable for relatively lean patients wherein the thickness of the anatomical tissue being sutured is not as great. The angle A for guide members 14a and 14b on the collar 12 can be varied or changed in order to obtain a desired suture stitch or closure length and width for different tissue thicknesses. Where there is no angle A between the longitudinal axes X' of the guide members and the central longitudinal axis X, such as when the central longitudinal axes X' are parallel to the central longitudinal axis X, the suture stitch or closure will have no width since each entry point will be vertically aligned with its corresponding exit point.

Figure 10:
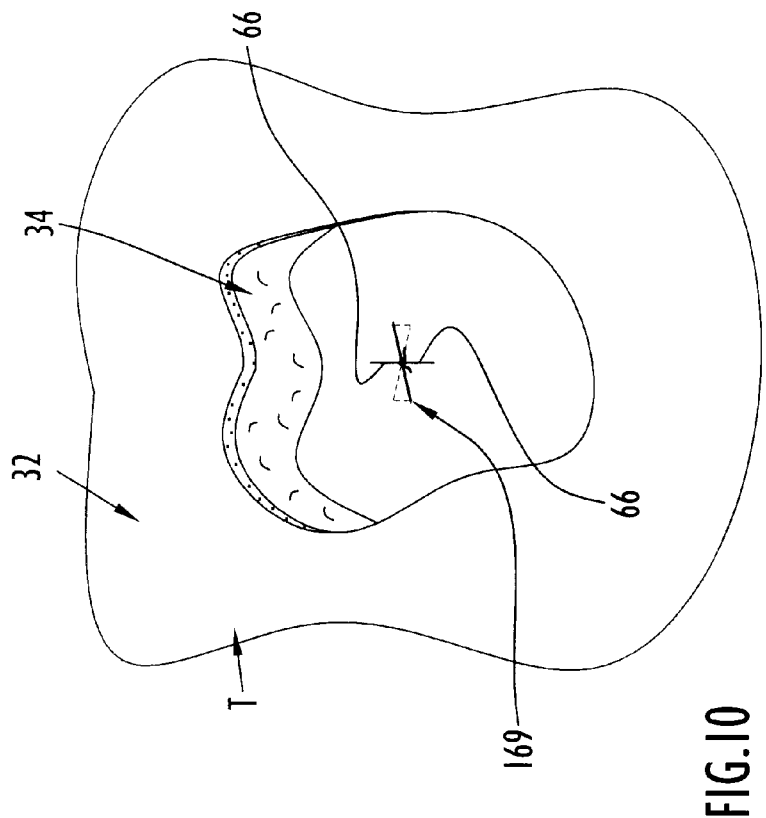
FIG. 10 is a broken top view illustrating a smaller size suture stitch capable of being formed in the anatomical tissue with a modified puncture site closure apparatus according to the present invention.

FIG. 10 illustrates a suture stitch or closure 169 having a length and width, also exaggerated for clarity, smaller or less than the length and width of the suture stitch or closure 69, the smaller length and width having been obtained with a puncture site closure apparatus having guide members 14a and 14b disposed at a smaller predetermined angle A with the central longitudinal axis X of the collar 12.

FIG. 11 illustrates an alternative puncture site closure apparatus 110 for forming a plurality of suture stitches or closures at a puncture site or opening in anatomical tissue without the need for rotating the apparatus relative to the portal sleeve during use. The puncture site closure apparatus 110 is the same as puncture site closure apparatus 10 except that puncture site closure apparatus 110 includes two pairs of guide members. In particular, the apparatus 110 includes a first pair of guide members 114a and 114b, similar to guide members 14a and 14b, and a second pair of guide members 114c and 114d. The guide members 114c and 114d are similar to guide members 114a and 114b but are disposed on collar 112 at locations rotationally offset from guide members 114a and 114b. The guide members 114a and 114b are disposed at diametrically opposite locations on collar 112 and are thusly disposed 180° from each other. The guide members 114c and 114d are disposed at diametrically opposite locations on collar 112 and are also disposed 180° from each other. The guide members 114a, 114b, 114c and 114d receive a penetrating member or needle by which first, second, third and fourth lengths of suture material, respectively, are passed through a designated layer or layers of tissue as described above. In this manner, a first suture stitch or closure can be formed at a puncture site with the first and second lengths of suture material, and a second suture stitch or closure can be formed at the puncture site with the third and fourth lengths of suture material.

FIG. 12 is illustrative of a puncture site closure procedure performed in the thoracic cavity of a patient. FIG. 12 illustrates a suture stitch or closure 269 formed in the thoracic cavity wall W' to close a puncture site or opening previously formed in the thoracic cavity wall W' to provide access to the thoracic cavity C'. In the case of thoracic cavity C', the wall W' includes external tissue layer or skin 232, intermediate tissue layer 234 including subcutaneous tissue or fat and inner tissue layer 236 comprising internal investing fascia 235, muscle layers 237 and pleura 238 with ribs 239 within muscle layers 237. The suture stitch or closure 269 is formed in substantially the same manner as that described for formation of suture stitch or closure 69; and, accordingly, a description of the specific procedural steps will not be repeated. The suture stitch or closure 269 begins at a selected depth or thickness portion of intermediate tissue layer 234. The selected depth or thickness portion is superior to the internal investing fascia 235, and the first and second lengths of suture material 250 and 252 thusly extend through the depth or thickness portion of tissue layer 234, the internal investing fascia 235, muscle layers 237 and the pleura 238. Accordingly, the knot 264 is disposed internally of the pleura 238 while the knot 268 is disposed within the intermediate tissue layer 234.

In view of the above, it should be appreciated that a plurality of puncture site closure apparatus can be provided, with each puncture site closure apparatus providing a different length and width for a suture stitch or closure to be obtained therewith. For instance, a plurality of puncture site closure apparatus can be provided, with each having a different predetermined angle A for the guide members thereof in order to obtain suture stitches or closures of different lengths and widths. In this manner, a puncture site closure apparatus for obtaining a suture stitch or closure of particular length and width can be optimally selected for use with a specific patient in accordance with the thickness of the anatomical tissue to be sutured or closed. It should also be appreciated that the puncture site closure apparatus can be inverted or turned upside down for use in either position.

With the apparatus, kit and methods for puncture site closure in accordance with the present invention, sutures are placed in anatomical tissue adjacent a puncture site or opening in the tissue while a portal sleeve is disposed in the opening. The sutures are placed in an anatomical wall of an anatomical cavity while a pneumoperitoneum is maintained in the anatomical cavity, the pneumoperitoneum providing protection for internal organs against inadvertent or unintentional penetration by the penetrating member through which the sutures are passed. Puncture sites or openings in anatomical tissue can be efficiently and properly sutured or closed by surgeons of varying degrees of skill and experience in that the guide members provide predetermined, positive guidance for the penetrating members. The puncture site closure apparatus according to the present invention can have the guide members thereof disposed on the collars at various angles in order to place the sutures in the tissue an optimal distance from the opening. A plurality of puncture site closure apparatus according to the present invention can be provided or supplied with each being capable of obtaining a different size suture stitch or closure therewith. Accordingly, the present invention allows a puncture site closure apparatus to be optimally selected in accordance with the anatomical characteristics of a particular patient. Suture stitches or closures formed in accordance with the present invention begin at a desired depth in the tissue and/or at a selected tissue layer. The present invention greatly increases the safety and efficacy of minimally invasive procedures in general and, in particular, minimally invasive procedures utilizing relatively large portal sleeves. The mechanical and operational simplicity encourages the suturing of an inner tissue layer or layers to close even relatively small size puncture sites or openings so as to improve the outcome of minimally invasive procedures in general.

Inasmuch as the present invention is subject to various modifications, variations and changes in detail, it is intended that all subject matter discussed above or shown in the accompanying drawings be interpreted as illustrative only and not be taken in a limiting sense.

What is claimed is:

1. A puncture site closure apparatus for placing sutures in anatomical tissue adjacent an opening in the anatomical tissue through which a portal sleeve extends comprising
   a collar for being disposed on the portal sleeve and having a central longitudinal axis and a cavity for receiving a portal sleeve to extend longitudinally through said collar; and
   a pair of guide members disposed on opposite sides of said collar, each of said guide members having upper and lower open ends and a lumen extending longitudinally therethrough, said collar being longitudinally movable relative to and along the portal sleeve to move said lower ends of said guide members a selected depth into an opening in anatomical tissue through which the portal sleeve extends, each of said lumens being adapted to removably, slidably receive a hollow penetrating member therethrough such that the penetrating member is guided by said guide members, respectively, to enter the anatomical tissue at entry points, respectively, located the selected depth in the anatomical tissue and to exit the anatomical tissue at exit points, respectively, on the anatomical tissue such that first and second lengths of suture material can be passed through the penetrating member and said guide members, respectively, to extend through a thickness portion of the anatomical tissue between the entry points and the exit points, respectively, on opposite sides of the opening, the first and second lengths of suture material remaining in the thickness portion of the tissue, following removal of the penetrating member therefrom, for use in suturing the opening closed following removal of the portal sleeve from the opening.

2. The puncture site closure apparatus as recited in claim 1 wherein said collar is longitudinally movable relative to and along the portal sleeve to move said lower ends of said guide members into the opening so that said lower ends are in contact with a selected layer of the tissue.

3. The puncture site closure apparatus as recited in claim 2 wherein each of said guide members has a central longitudinal axis and said central longitudinal axes of said guide members are disposed at a predetermined angle to said central longitudinal axis of said collar.

4. The puncture site closure apparatus as recited in claim 3 wherein said central longitudinal axes of said guide members are angled in directions opposite one another.

5. The puncture site closure apparatus as recited in claim 4 wherein said central longitudinal axes of said guide members are disposed in firs t planes, respectively, parallel to a second plane containing said central longitudinal axis of said collar, said central longitudinal axes of said guide members being disposed within said first planes, respectively, at said predetermined angle to a third plane, said third plane being perpendicular to said first and second planes and containing said central longitudinal axis of said collar.

6. The puncture site closure apparatus as recited in claim 5 wherein said central longitudinal axis of one of said guide members is angled in a first direction to define said angle with said third plane and said central longitudinal axis of the other of said guide members is angled in a second direction, opposite said first direction, to define said angle with said third plane.

7. The puncture site closure apparatus as recited in claim 1 wherein said angle is in the range of 3 to 20 degrees.

8. The puncture site closure apparatus recited in claim 7 wherein said lower ends are disposed in a plane and said angle dictates a predetermined radial distance, within said plane of said lower ends, between said central longitudinal axes of said guide members, respectively, and said central longitudinal axis of said collar.

9. The puncture site closure apparatus as recited in claim 8 wherein said angle dictates to said predetermined radial distance between the entry points, respectively, and a central longitudinal axis of the portal sleeve.

10. The puncture site closure apparatus as recited in claim 9 wherein said angle dictates to said predetermined radial distance between the entry points and a center of the opening.

11. The puncture site closure apparatus as recited in claim 10 wherein said central longitudinal axes of said guide members are disposed in fourth planes, respectively, disposed at said angle with said third plane, said fourth planes intersecting one another at a location centrally located between said upper and lower ends.

12. The puncture site closure apparatus as recited in claim 11 wherein said collar has a length between said upper and lower ends and a longitudinal gap is formed in said collar extending along the entirety of said length, said gap communicates with said cavity to allow passage of the portal sleeve through said gap into said cavity.

13. The puncture site closure apparatus as recited in claim 12 wherein said collar has a non-expanded position wherein said gap has an initial gap width and said cavity has an initial cavity size, said collar is movable from said non-expanded position to an expanded position wherein said gap has a second gap width, greater than said initial gap width, and said cavity has a second cavity size, greater than said initial cavity size, to permit passage of the portal sleeve through said gap into said cavity, and said collar is movable from said expanded position toward said non-expanded position to retain the portal sleeve with said cavity.

14. The puncture site closure apparatus as recited in claim 13 wherein said cavity has an initial cavity size smaller than an external cross-sectional size of the portal sleeve such that said collar compressively grips the portal sleeve received in said cavity.

15. The puncture site closure apparatus as recited in claim 14 wherein said collar is resiliently biased toward said non-expanded position.

16. A kit for forming and thereafter closing an opening in anatomical tissue in a minimally invasive procedure comprising
    a penetrating instrument including a portal sleeve having a lumen therethrough and an obturator disposed in said lumen, said portal sleeve having a central longitudinal axis, a distal end for disposition internally of the anatomical tissue and a proximal end for disposition externally of the tissue, said obturator having a distal end for penetrating the tissue, said distal end of said obturator protruding distally beyond said distal end of said portal sleeve whereby an opening is formed in the tissue by penetration of said obturator therethrough and said portal sleeve extends through the opening, said obturator being withdrawable from said portal sleeve, upon disposition of said distal end of said portal sleeve internally of the tissue, such that said portal sleeve remains in the opening with said lumen of said portal sleeve establishing communication through the tissue from externally to internally thereof; and
    a puncture site closure apparatus for being removably, slidably disposed on said portal sleeve and including a collar having a cavity for receiving said portal sleeve such that said portal sleeve extends longitudinally through said collar, and a pair of guide members disposed at opposing locations on said collar at a predetermined angle to said central longitudinal axis of said portal sleeve, said guide members being angled in opposite directions, each of said guide members having upper and lower open ends and a passage extending longitudinally therethrough, said passages being adapted to receive a hollow penetrating member for penetrating the anatomical tissue, said guide members guiding the penetrating member into and through the anatomical tissue such that lengths of suture material can be passed through the tissue via the penetrating member and said guide members, respectively, for use in forming a suture stitch to close the opening upon removal of said portal sleeve therefrom.

17. The kit as recited in claim 16 wherein said guide members have central longitudinal axes, respectively, said central longitudinal axes of said guide members being disposed in planes, respectively, that diagonally cross one another at a location between said upper and lower open ends.

18. The kit as recited in claim 17 wherein said planes of said central longitudinal axes of said guide members each define said predetermined angle with said central longitudinal axis of said portal sleeve.

19. The kit as recited in claim 16 wherein said collar is longitudinally, slidably movable relative to and along said portal sleeve to position said lower ends of said guide members within the opening in contact with a selected layer of the tissue such that the penetrating member, as guided by said guide members, penetrates the tissue at entry points, respectively, on the selected layer.

20. The kit as recited in claim 16 wherein said collar is longitudinally, slidably movable relative to and along said portal sleeve to position said lower ends of said guide members a selected depth within the opening such that the penetrating member, as guided by said guide members, penetrates the tissue at entry points, respectively, located the selected depth in the tissue.

21. The kit as recited in claim 18 wherein said predetermined angle dictates a predetermined length for the suture stitch.

22. The kit as recited in claim 21 wherein said angle is in the range of 3 to 20 degrees.

23. A method of closing an opening in anatomical tissue through which a portal sleeve extends comprising the steps of
    moving a collar of a puncture site closure apparatus along the portal sleeve, while the portal sleeve is disposed in the opening, to position open lower ends of guide members, carried by the collar, adjacent the anatomical tissue at selected locations spaced outwardly from the opening;
    inserting a hollow penetrating member into a lumen of one of the guide members;
    advancing the penetrating member within the lumen of the one guide member to penetrate the anatomical tissue, at an entry point on the anatomical tissue, with an open distal end of the penetrating member;
    moving the penetrating member through the tissue, as guided by the one guide member, to cause the open distal end of the penetrating member to exit the tissue internally at an exit point on the tissue;
    passing a length of filamentous suture material through the penetrating member so that a first end of the length of suture material protrudes internally of the tissue through the open distal end of the penetrating member and a second end of the length of suture material is disposed externally of the tissue;
    introducing a grasping instrument through a lumen of the portal sleeve to position a distal end of the grasping instrument internally of the tissue;
    grasping the length of suture material internally of the tissue with the distal end of the grasping instrument;
    removing the penetrating member from the tissue leaving the length of suture material extending through the tissue;
    withdrawing the grasping instrument from the portal sleeve so that the first end of the length of suture material is drawn externally of the tissue;
    repeating said inserting, said advancing, said moving the penetrating member, said passing, said introducing, said grasping, said removing and said withdrawing steps on the other guide member to place another length of suture material in the anatomical tissue;

tying the first ends of the lengths of suture material together, externally of the tissue, to form a knot;

passing the knot through the portal sleeve to dispose the knot internally of the tissue;

withdrawing the portal sleeve from the opening;

pulling the second ends of the length of suture material to approximate the anatomical tissue at the opening; and tying the second ends of the lengths of suture material together to form a knot externally of the entry points whereby a suture stitch of desired tension is formed in the tissue with the lengths of suture material.

24. The method of closing an opening as recited in claim 23 wherein said step of moving the penetrating member includes guiding the penetrating member with the guide member to follow a predetermined angle through the tissue.

25. The method of closing an opening as recited in claim 24 wherein said step of guiding includes guiding the penetrating member to follow a predetermined angle in the range of 3 to 20 degrees relative to a central longitudinal axis of the portal sleeve.

26. The method of closing an opening as recited in claim 23 wherein said step of moving the collar includes positioning the lower ends a selected depth in the tissue.

27. The method of closing an opening as recited in claim 23 wherein said step of moving the collar includes positioning the lower ends adjacent a selected layer of the tissue.

28. The method of closing an opening as recited in claim 27 wherein the anatomical tissue is the abdominal cavity wall, said step of moving the collar includes positioning the lower ends close to the internal investing fascia and said step of moving the penetrating member includes moving the penetrating member through the internal investing fascia, the underlying muscle layer and the peritoneum to exit the abdominal cavity wall at the exit point on the peritoneum.

29. The method of closing an opening as recited in claim 28 wherein said step of advancing includes penetrating the abdominal cavity wall at the entry point on the subcutaneous tissue layer of the abdominal cavity wall and said step of moving the penetrating member includes moving the penetrating member through a thickness portion of the subcutaneous tissue layer prior to penetration of the internal investing fascia by the penetrating member.

30. The method of closing an opening as recited in claim 27 wherein the anatomical tissue is the thoracic cavity wall, said step of moving the collar includes positioning the lower ends close to the internal investing fascia and said step of moving the penetrating member includes moving the penetrating member through the internal investing fascia, the underlying muscle layer and the pleura to exit the thoracic cavity wall at the exit point on the pleura.

31. The method of closing an opening as recited in claim 30 wherein said step of advancing includes penetrating the thoracic cavity wall at the entry point on the subcutaneous tissue layer of the thoracic cavity wall and said step of moving the penetrating member includes moving the penetrating member through a thickness portion of the subcutaneous tissue layer prior to penetration of the internal investing fascia by the penetrating member.

32. The method of closing an opening as recited in claim 23 wherein the anatomical tissue is a wall of an anatomical cavity and further including, prior to said step of moving the collar, the step of creating a pneumoperitoneum in the anatomical cavity to provide increased space therein.

* * * * *